United States Patent [19]
Kolff et al.

[11] Patent Number: 5,282,849
[45] Date of Patent: Feb. 1, 1994

[54] VENTRICLE ASSIST DEVICE WITH VOLUME DISPLACEMENT CHAMBER

[75] Inventors: Willem J. Kolff, Salt Lake City, Utah; Yvo M. Smulders, Amsterdam, Netherlands; Paul D. Diegel, Sandy, Utah; James W. Long, Jr., Salt Lake City, Utah; Donald B. Olsen, Salt Lake City, Utah; John W. Holfert, Bountiful, Utah

[73] Assignee: University of Utah Research Foundation, Salt Lake City, Utah

[21] Appl. No.: 811,455

[22] Filed: Dec. 19, 1991

[51] Int. Cl.$^5$ ................ A61M 1/10; A61M 1/362; F04B 17/00
[52] U.S. Cl. .................................. 623/3; 600/16; 417/413 R
[58] Field of Search ............... 600/16–18; 623/3; 417/393, 395, 413

[56] References Cited

U.S. PATENT DOCUMENTS

| | | | |
|---|---|---|---|
| 3,568,214 | 3/1971 | Goldschmied | 600/16 X |
| 3,633,217 | 1/1972 | Lance | 623/3 |
| 4,173,796 | 11/1979 | Jarvik | 623/3 |
| 4,177,523 | 12/1979 | Lande | 623/3 |
| 4,240,409 | 12/1980 | Robinson et al. | 623/3 |
| 4,250,872 | 2/1981 | Tamari | 600/16 |
| 4,512,726 | 4/1985 | Strimling | 600/16 X |
| 4,524,466 | 6/1985 | Hall et al. | 600/16 X |
| 4,557,673 | 12/1985 | Chen et al. | 600/16 X |
| 4,838,889 | 6/1989 | Kolff | 623/3 |
| 4,888,011 | 12/1989 | Kung et al. | 600/16 X |
| 4,994,078 | 2/1991 | Jarvik | 623/3 |
| 5,041,132 | 8/1991 | Miyata | 623/3 |
| 5,089,016 | 2/1992 | Millner et al. | 623/3 |
| 5,092,878 | 3/1992 | Miyata | 623/3 |
| 5,092,879 | 3/1992 | Jarvik | 623/3 |

FOREIGN PATENT DOCUMENTS

| | | | |
|---|---|---|---|
| 1450828 | 1/1989 | U.S.S.R. | 600/16 |
| 8904644 | 6/1989 | World Int. Prop. O. | 623/3 |
| 9007648 | 7/1990 | World Int. Prop. O. | 623/3 |

Primary Examiner—Randall L. Green
Assistant Examiner—Elizabeth M. Burke
Attorney, Agent, or Firm—Thorpe, North & Western

[57] ABSTRACT

A ventricle assist device for placement within a living body and including a self contained drive motor for generating pumping action with respect to a hydraulic pumping fluid. The ventricle assist device includes a ventricle having a blood chamber and a pumping chamber and an interconnect means coupled to the pumping chamber of the ventricle for receiving and displacing hydraulic fluid. A separate volume displacement chamber is attached to the interconnect means and provides a reservoir for excess hydraulic fluid for storage during diastole. A fluid pump and drive motor is positioned within the volume displacement chamber and connected at the interconnect means to supply the required pumping action for transfer of hydraulic fluid to and from the pumping chamber. Placement of the fluid pump and drive motor within the volume displacement chamber provides enhanced dissipation of heat from the energy conversion system and improved performance and durability.

21 Claims, 2 Drawing Sheets

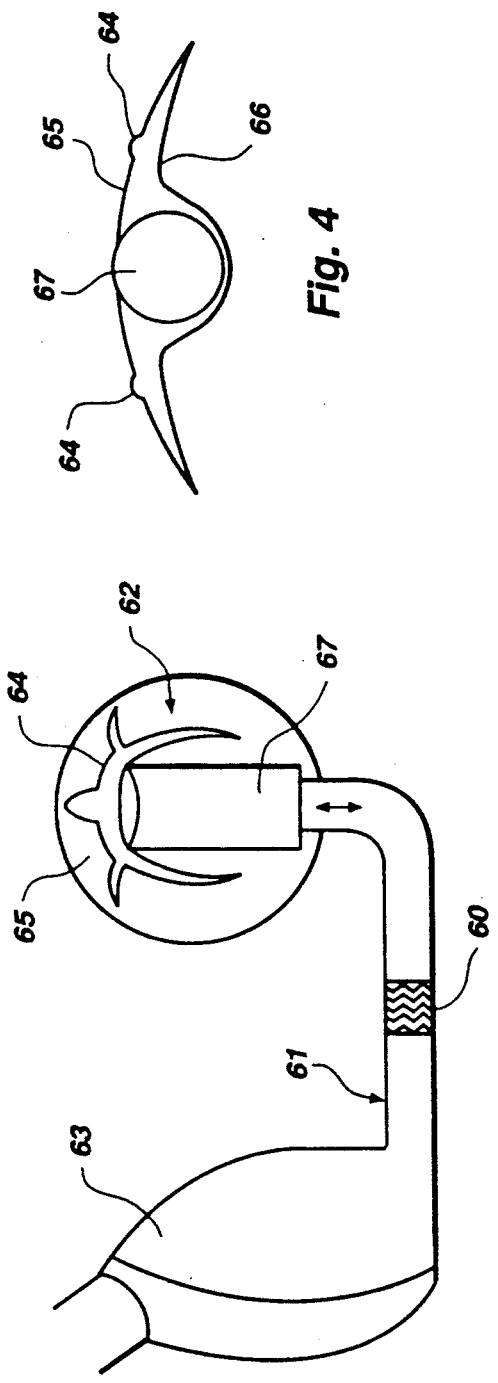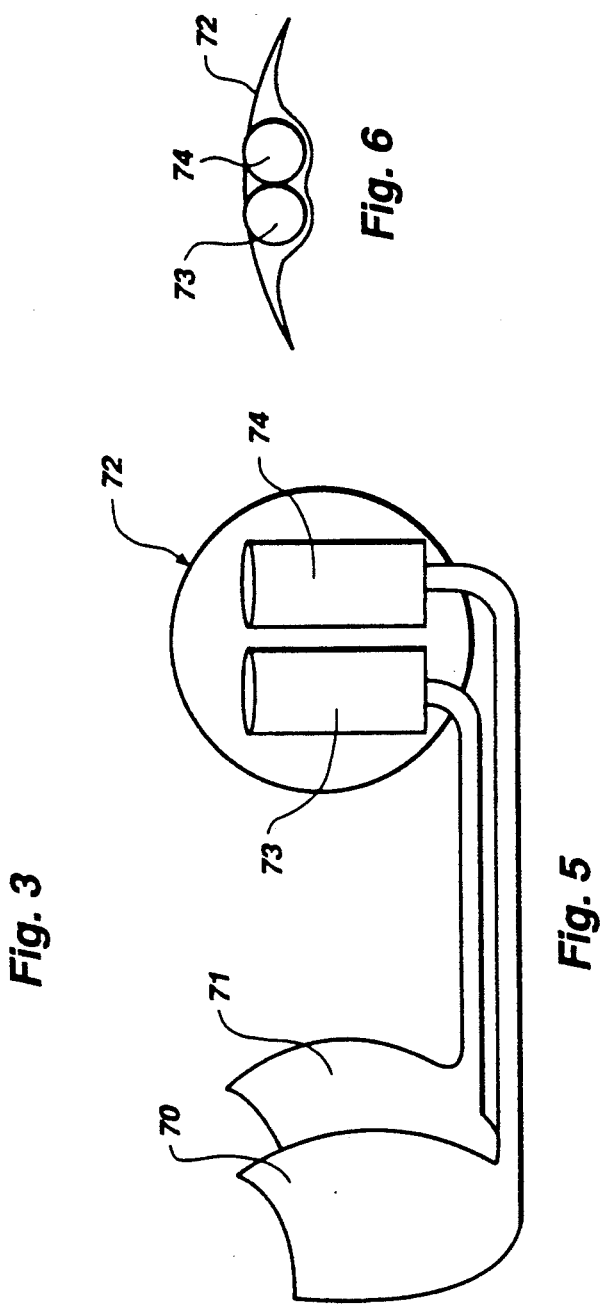

VENTRICLE ASSIST DEVICE WITH VOLUME DISPLACEMENT CHAMBER

This invention was funded in part by a grant from the National Institute of Health under contract number NO1-HV-88106.

BACKGROUND OF THE INVENTION

1. Field of the Invention

This invention relates to a device and method for providing pumping support to an artificial ventricle or heart. More particularly, the present invention pertains to a hydraulic pumping system used in connection with an artificial ventricle which relies on transfer of hydraulic fluid between a pumping chamber associated with the ventricle and a volume displacement chamber which is separated from the pumping chamber and associated ventricle.

2. Prior Art

Current trends in research in the general field of ventricle assist devices and artificial hearts is placing greater emphasis on electrohydraulic drive systems instead of air-driven mechanisms which require use of a driveline through the skin. The advantages of an electrohydraulic heart are numerous. The total unit is implantable and self-contained. In contrast, pneumatic drive systems are cumbersome and impose serious constraints in view of the transcutaneous driveline and potential for infection.

An early design for an electrohydraulic drive system is set forth in U.S. Pat. No. 4,173,796 by Jarvik. It discloses the use of an axial impeller assembly with an electric drive motor, referred to hereafter as a "fluid pump and drive motor". Hydraulic fluid is moved by action of the impeller assembly as it rotates about its axis. By reversing the electric motor, the hydraulic fluid can be reversibly pumped, thereby filling and extracting the fluid with respect to a pumping chamber associated with the ventricle.

When used within a total artificial heart, the fluid pump and drive motor can simple be reversed to transfer fluid from a first pumping chamber associated with a left ventricle, to a second pumping chamber associated with the right ventricle. The difference in cardiac output between the left and right ventricles can be balanced by use of an intra-atrial shunt, a leaking pulmonary artery valve or a small extra compliance reservoir.

In situations where the pumping fluid is not alternately driving a blood pumping chamber, a volume displacement chamber is used to store this pumping fluid. For example, during diastole in a single ventricle assist device, pumping fluid is removed from the pumping chamber associated with the ventricle through a conduit, and is stored in a bag or other volume displacement chamber. This transfer is accomplished with the same type of reversible fluid pump and drive motor as is disclosed in the Jarvik patent. During systole, the motor reverses and forces the fluid from the displacement chamber to the pumping chamber with the ventricle.

Prior practice in positioning the fluid pump and drive motor has followed the pattern set by the Jarvik patent. Specifically, this device is placed in the intermediate flow line or interconnect between the pumping chamber and the volume displacement chamber. This is a logical position because the fluid must pass through the impeller assembly of the pump, which naturally becomes part of the flow path. Accordingly, prior art practice has consistently positioned the fluid pump and drive motor as a continuous part of the interconnect device, or as a continuous part of the interconnect flow path. As such, hydraulic fluid contact has been limited to the interior flow channel within the fluid pump. The exterior surface of the fluid pump and drive motor have been treated much like a tubular enclosure in that this exterior structure functioned to contain the fluid within the flow path. Therefore, any contact of hydraulic fluid with the exterior of the interconnect and associated fluid pump was contrary to reasonable design considerations.

The use of an electrohydraulic drive system involves other mechanical considerations which are not associated with a pneumatic drive system. For example, because the system is self-contained within the patient, dependability and durability are critical. Both of these factors are affected by the minimization of wear on components of the drive motor. Accordingly, a variety of techniques have been applied to design drive motors with a minimal amount of friction, as well as other mechanical factors that cause abrasive wear and generate attendant heat.

Although advanced technology has provided much improved motor design, there remains the challenge of dissipating heat generated with the drive motor. It will be apparent to those skilled in the art that electrohydraulic drive systems depend on conversion of electric power to hydraulic power. Such conversions will always generate some heat as a by product. When such heat is confined and accumulated within the small volume of a pumping system in support of a ventricle, some detrimental effect is inevitable. In prior art systems where the drive motor and impellers are further confined within a tubular interconnect, dissipation of heat is even more difficult. Without effective heat control, increased wear occurs and the inevitable failure of the system is accelerated.

OBJECTS AND SUMMARY OF THE INVENTION

It is therefore an object of the present invention to provide improved means for dissipating heat within a ventricle assist device utilizing an electrohydraulic drive system.

A further object of the present invention is to provide improved efficiency in a fluid delivery system to an artificial ventricle pumping membrane.

A still further object of this invention is to provide an improved electrohydraulic drive system which requires less space within the ventricle assist device, thereby facilitating emplacement within a patient and simplifying surgical procedures.

These and other objects are realized in a ventricle assist device for placement within a living body which includes a self contained drive motor for generating pumping action with respect to a hydraulic pumping fluid being reversibly transferred to and from a pumping chamber for effecting blood transfer. This device is comprised of a ventricle housing and an internal pumping membrane which divides the ventricle into a blood chamber and a pumping chamber. The blood chamber includes inlet and outlet means for enabling unidirectional blood flow to and from the ventricle. A separate volume displacement chamber having sufficient fluid volume to receive the pumping fluid from the pumping chamber is attached to the ventricle by means of interconnect means which define a fluid flow channel there-between. A fluid pump and drive motor is positioned at the interconnect means and is substantially within the volume of the displacement chamber such that a substantial exterior portion of the pump and drive motor is contacted by the hydraulic pumping fluid contained therein. This device can also be structured with respect to a clamshell pumping mechanism in which the clamshell provides a ventricle support housing and an internal pumping membrane which forms an exposed flexible pumping diaphragm which is powered by the fluid pump and drive motor. Here again, the fluid pump and drive motor are positioned within a separate volume displacement chamber wherein a substantial exterior portion of the pump and drive motor is contacted by the hydraulic fluid within the displacement chamber.

Other objects and features of the present invention will be apparent to those skilled in the art in view of the following detailed description, in combination with the accompanying drawings.

DESCRIPTION OF DRAWINGS

FIG. 3 shows a schematic representation of an additional embodiment of the inventive ventricle assist device.

FIG. 4 is a cross-section taken along the lines 4—4 of FIG. 3.

FIG. 5 is a schematic representation of a further embodiment of the present invention wherein two ventricle assist devices are coupled to a single volume displacement chamber.

FIG. 6 is a cross-section taken along the lines 6—6 of FIG. 5.

DETAILED DESCRIPTION OF THE INVENTION

Figure 1:
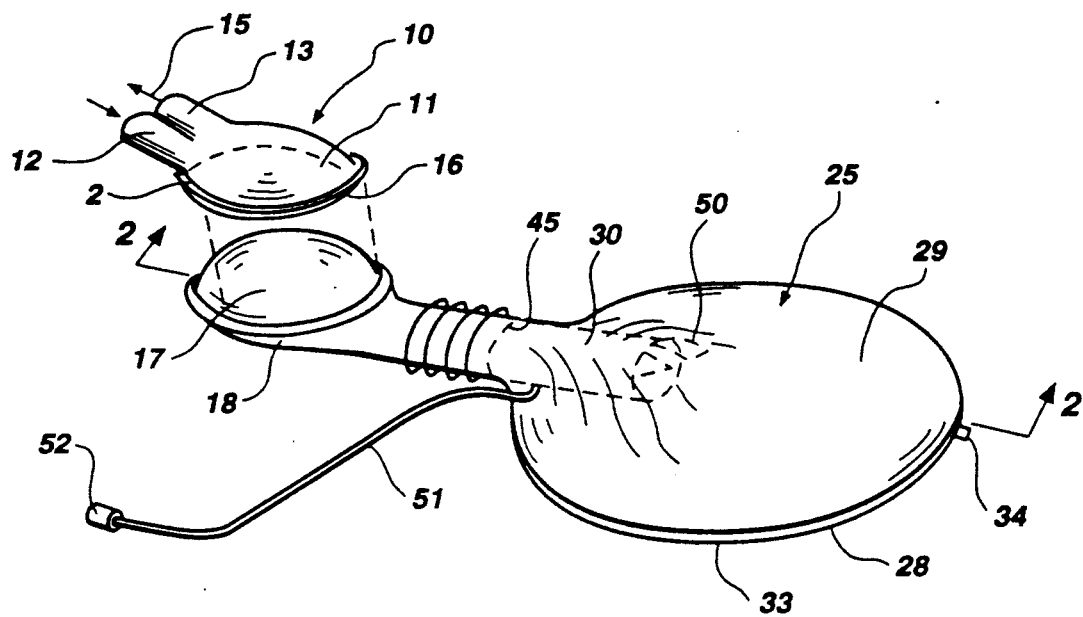
FIG. 1 is a elevated perspective view of a ventricle assist device constructed in accordance with the present invention.
Figure 2:
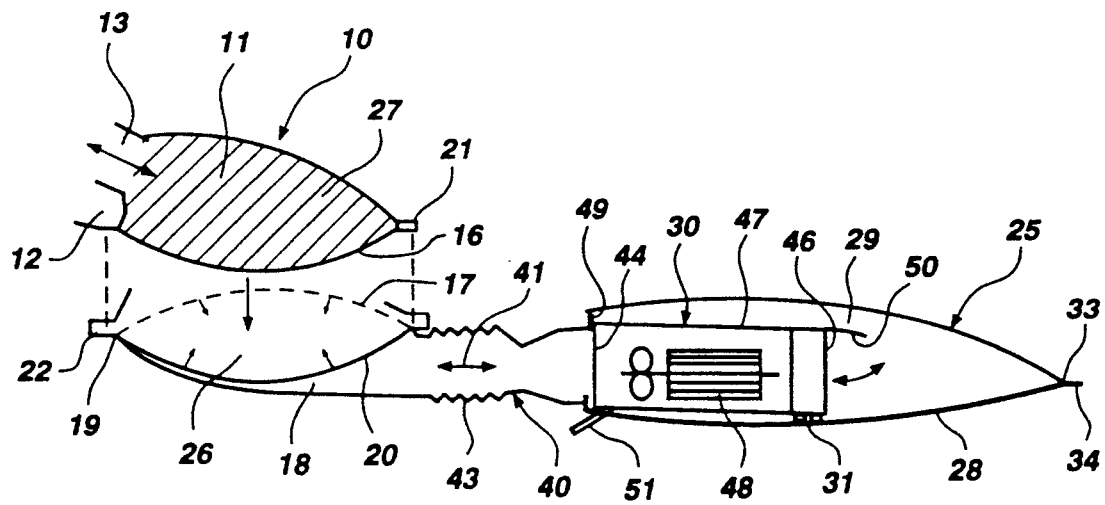
FIG. 2 is a graphic representation of a cross-section taken along the lines 2—2 in FIG. 1.

FIGS. 1 and 2 illustrate a ventricular assist device comprising a ventricle which consists of a ventricle housing 11 which encloses a blood chamber and includes inlet 12 and outlet 13 for enabling unidirectional blood flow 15 to and from the ventricle 10. The base 16 of the ventricle comprises a flexible membrane which cooperates with a pumping membrane 17 to alternately extend and collapse in accordance with conventional practice. The embodiment illustrated in FIG. 1 is generally characterized as a clamshell structure because the ventricle 10 is structured as a soft polymer, compliant blood sack. The more rigid pumping structure is supplied by the shell portion of the ventricle assist device which consists of a more rigid structure 18 formed as a concave support (see FIG. 2). The flexible pumping diaphragm 17 is sealed at the periphery 19 of the rigid shell and provides the pumping force required by extending (shown in phantom line) and collapsing 20 in a reciprocating manner.

In practice, the soft ventricle 10 is first sutured in place within the patient and tested for operational integrity to ensure that there are no leaks in the system and to verify that the ventricle is operational. At that point, the shell portion 18 and pumping support system are added by nesting the soft ventricle 10 within the concave shell 18. A stiff interlock perimeter 21 which extends around the soft ventricle 10 seats within a retaining ring 22 as illustrated in FIG. 2. In this configuration, the contacting membrane 16 of the blood chamber reciprocates inward and outward in response to corresponding movement of the pumping membrane 17. The components of the ventricle 10 and clamshell 18 are made by vacuum forming polyurethane and by radio frequency welding perimeters to develop the required structures. Ventricle sizes depend on the needs of a patient, but are typically in the range of 60 to 100 cc.

It is apparent in this configuration that a separate volume displacement chamber 25 is required to receive the pumping fluid during diastole, when the pumping membrane 17 is retracted to its collapsed position 20. This separate volume displacement chamber 25 must have sufficient fluid volume to receive the pumping fluid from the pumping chamber 26 when the blood chamber 27 is in diastole and the pumping chamber is at its minimal volume (as illustrated in FIG. 2). The illustrated volume displacement chamber 25 is configured as a disc with opposing first 28 and second 29 exterior faces of convex configuration when fluid volume is full. One of these convex faces 28 comprises rigid material for maintaining the disc configuration and for providing support to a fluid pump and drive motor (referred to collectively as 30) which may be secured 31 to the rigid face 28. This rigid face or back plate 28 was formed of a thick sheet of polyurethane of about 0.180 inches. It is also possible to fabricate the volume displacement chamber 25 with a soft back 28 inasmuch as maintenance of any particular disc configuration is not essential to operation of the system.

The opposing face of the volume displacement chamber 25 comprises a flexible member 29 which is capable of readily collapsing in response to evacuation of a substantial portion of the fluid into the pumping chamber 26. This desired compliance can be embodied with a sheet fabricated of polyurethane and appropriately sealed at the disc perimeter 33. This perimeter 33 is also provided with an access port 45 which facilitates initial filling of the volume displacement chamber with hydraulic fluid, as well as making adjustment in fluid volume at a later time.

The pumping chamber 26 and volume displacement chamber 25 are coupled together by an interconnect means 40 which defines a fluid flow channel 41 enabling delivery of pumping fluid between the displacement chamber 25 and the pumping chamber 26. The configuration and length of the interconnect means 40 is selected to permit placement of the ventricle 10 and pumping chamber 26 in proximity to the patient's cardiac cavity, with the volume displacement chamber 25 being disposed in the thorax or abdomen. Specifically, the volume displacement chamber is configured to fit against the human rib cage in the dorsal part of the phrenicocostal sinus. The neck is made flexible 43 to facilitate positioning of the volume displacement chamber 25 within the patient.

The primary feature of the present invention involves the placement of the fluid pump and drive motor 30 within the volume displacement chamber 25, rather than within the interconnect means 40. The fluid path 41 through the interconnect is maintained into the fluid pump and drive motor 30 by attachment of the proximal end 44 of the fluid pump at the interconnect means 45, with the distal end 46 being positioned within the displacement chamber for providing reversible pumping action to transfer hydraulic fluid through the interconnect means and between the displacement chamber and the pumping chamber. The fluid pump and drive motor is positioned substantially within the volume displacement chamber such that a substantial exterior portion 47 of the fluid pump and drive motor is contacted by hydraulic fluid contained within the volume displacement chamber.

The illustrated fluid pump and drive motor comprises an axial flow pump in which the exterior portion 47 is fabricated of heat transfer material which enhances thermal transfer of energy from the drive motor 48 into the hydraulic fluid contained within the volume displacement chamber. For preferred efficiency, at least one half of the exterior portion of the fluid pump and drive motor 30 should be contained within the volume displacement chamber and in contact with the hydraulic fluid. A vacuum formed ring 49 comprised of polyurethane keeps the motor in place at its point of attachment to the interconnect means. A strain relief flap 50 is provided adjacent to the distal end of the fluid pump and drive motor to protect the compliance membrane 29 from folding over the distal end 46 of the fluid pump. This ensures that this membrane is not sucked into the fluid pump as hydraulic fluid is being returned to the pumping chamber 26.

The size of the drive motor 30 is configured to be slightly smaller than an inner diameter of the tubular interconnect 40 to facilitate sealing at the vacuum formed ring 49. Power supply wires 51 leave the volume displacement chamber through a small tube which has a side tube connected to it, proximal to where it is sealed to the electric plug. The free end 52 of the side tube can be occluded with a plug and buried under the skin so that it can be retrieved if necessary. This tube can also be used to fill and de-air the volume displacement chamber, as well as change the hydraulic fluid volume after implantation of the device. It is also possible to take pressure recordings from the volume displacement chamber at the end of this tube 52. The wire tube leaves the skin using a skin button as is well known in this field of art, particularly with the use of pneumatic drive lines. The system can be made completely implantable by the use of transcutaneous energy transfer systems, which are currently under development.

It will be apparent to those skilled in the art that the preferred embodiment set forth in FIGS. 1 and 2 is merely an exemplary of the inventive emplacement of positioning the fluid pump and drive motor within the volume displacement chamber. In addition, additional embodiments are illustrated in FIGS. 3 through 6.

FIG. 3 illustrates the use of a coupling element 60 within the interconnect line 61. This facilitates attachment and detachment of the volume displacement chamber 62 without the need of concurrently removing the ventricle 63. This figure also illustrates the use of a crows foot indentation 64 wherein the rigid material comprising one of the convex faces of the disc members includes a channel indentation 64 projecting away from the volume displacement chamber (see FIG. 4) to provide fluid flow paths for the hydraulic fluid as the compliant face 66 seats toward the rigid convex face 65. The fluid pump and electric motor 67 is illustrated at its central position within this volume displacement chamber 62.

FIGS. 5 and 6 illustrate the use of a single volume displacement chamber for servicing two separate ventricles 70 and 71. In this case, the volume displacement chamber 72 includes separate fluid pumps and drive motors 73 and 74. Although less chamber volume is available, the alternating fill and extraction cycles of the respective motors 73 and 74 provide adequate hydraulic fluid to maintain pumping operations. Operational aspects of both embodiments shown in FIGS. 3 and 5 are in accordance with previous discussion.

In all instances, the present invention provides several significant advantages over the prior art. First, by placement of the energy convertors or drive motors within the volume displacement chamber, more effective cooling of the energy convertors is provided. Heat is conducted away from the energy convertor into the volume displacement chamber or into the pumping chamber, where further heat dissipation is accomplished into the patient's body. Secondly, the placement of the energy converter within the volume displacement chamber reduces the size requirements for the total system. This facilitates compactness of the device and ease of emplacement within the patient. Both of these benefits have been verified in actual test situations within test animals. Sizing and placement considerations have been verified in cadavers. The invention appears to have immediate utility with respect to ventricle assist devices which are in constant demand. As the demand for permanent ventricle assist devices develops, the inventive ventricle assist device disclosed herein will be of even greater value, in view of its greater capacity to dissipate heat and survive extended use.

We claim:

1. A ventricle assist device for placement within a living body and including a self-contained drive motor for generating pumping action with respect to a hydraulic pumping fluid which is reversibly transferred to and from a pumping chamber for effecting blood transfer, said device comprising:

a ventricle comprised of a ventricle housing and an internal pumping membrane which divides the ventricle into a blood chamber and a pumping chamber, said blood chamber including inlet and outlet means for enabling unidirectional blood flow to and from the ventricle;

a separate volume displacement chamber structured as a collapsible bag without a pumping diaphragm and having sufficient fluid volume to receive pumping fluid from the pumping chamber when the blood chamber is in diastole and the pumping chamber is at minimal volume;

interconnect means coupled between the pumping chamber and the volume displacement chamber and defining a fluid flow channel for delivery of the pumping fluid between the displacement chamber and the pumping chamber of the ventricle; and a fluid pump and drive motor positioned at the interconnect means and being capable of reversible pumping action to transfer hydraulic fluid through the interconnect means and between the displacement chamber and the pumping chamber, said fluid pump and drive motor being positioned substantially within the volume displacement chamber such that a substantial exterior portion of the fluid pump and drive motor is contacted by the pumping fluid contained within the volume displacement chamber.

2. A device as defined in claim 1, wherein the fluid pump comprises an axial flow pump, said exterior portion of the pump and drive motor being comprised of heat transfer material which permits thermal transfer of energy from the drive motor into the hydraulic fluid contained within the volume displacement chamber.

3. A device as defined in claim 1, wherein at least half of the exterior portion of the fluid pump and drive motor is contained within the volume displacement chamber.

4. A device as defined in claim 1, wherein the fluid pump and drive motor includes a proximal end in relation to the pumping chamber and a distal end, said proximal end being attached and sealed at the interconnect means, a remaining portion of the fluid pump and drive motor being housed within the volume displacement chamber.

5. A device as defined in claim 4, further comprising strain relief means positioned adjacent to the distal end of the fluid pump and drive motor to prevent a wall portion which encloses the volume displacement chamber from being sucked into the fluid pump and drive motor.

6. A device as defined in claim 5, wherein the strain relief means comprises a flap attached to the distal end of the fluid pump and drive motor, said flap projecting beyond said distal end and being operable to restrain movement of the wall portion of the displacement chamber from collapsing against the distal end during systole.

7. A device as defined in claim 1, wherein the interconnect means comprises a tubular interconnect which is flexible and has sufficient length to permit placement of the ventricle in proximity to a patient's cardiac cavity and the volume displacement chamber in the area of a patient's thorax or abdomen.

8. A device as defined in claim 7, wherein the fluid pump and drive motor are positioned within a casing which has an outer diameter slightly smaller than an inner diameter of the tubular interconnect, said casing being positioned and sealed at a proximal end within the tubular interconnect to provide a flow path through the tubular interconnect and fluid pump to the volume displacement chamber.

9. A device as defined in claim 1, further comprising a second ventricle and associated second interconnect means coupled to the volume displacement chamber, and further including a second fluid pump and drive motor positioned at the second interconnect means and being capable of reversible pumping action to transfer hydraulic fluid through the second interconnect means and between the displacement chamber and the second pumping chamber of the second ventricle, said second pump and drive motor being positioned substantially within the volume displacement chamber such that a substantial exterior portion of the second pump and drive motor is contacted by the hydraulic fluid contained within the volume displacement chamber.

10. A device as defined in claim 1, wherein the volume displacement chamber is configured as a disc configuration with opposing first and second exterior convex faces, at least one of the exterior convex faces being compliant to permit expansion of volume contained within the volume displacement chamber for receiving hydraulic fluid contained therein.

11. A device as defined in claim 10, wherein the first exterior convex comprises rigid material for maintaining the disk configuration, the second exterior convex face being comprised of compliant material.

12. A device as defined in claim 11, wherein the first convex face comprised of rigid material includes channel indentation projecting away from the volume displacement chamber to provide fluid flow paths if the second convex face of complaint material seats towards the first convex face.

13. A ventricle assist device for use with a clamshell pumping mechanism within a living body and including a self-contained drive motor for generating pumping action with respect to a hydraulic pumping fluid which is reversibly transferred to and from a pumping chamber for effecting blood transfer, said device comprising:

a clamshell pumping mechanisms comprised of a ventricle support housing and an internal pumping membrane which forms an exposed flexible pumping diaphragm for a pumping chamber, said clamshell housing being configured to receive and removably retain an artificial ventricle which includes a blood chamber having inlet and outlet means for enabling unidirectional blood flow to and from the ventricle;

a separate volume displacement chamber structured as a collapsible bag without a pumping diaphragm and having sufficient fluid volume to receive pumping fluid from the pumping chamber when the blood chamber is in diastole and the pumping chamber is at minimal volume;

interconnect means coupled between the pumping chamber and the volume displacement chamber and defining a fluid flow channel for delivery of the pumping fluid between the displacement chamber and the pumping chamber of the ventricle; and a fluid pump and drive motor positioned at the interconnect means and being capable of reversible pumping action to transfer the pumping fluid through the interconnect means and between the displacement chamber and the pumping chamber, said pump and drive motor being positioned substantially within the volume displacement chamber such that a substantial exterior portion of the pump and drive motor is contacted by the pumping fluid contained within the volume displacement chamber.

14. A device as defined in claim 13, wherein the fluid pump comprises an axial flow pump, said exterior portion of the pump and drive motor being comprised of heat transfer material which permits thermal transfer of energy from the drive motor into the hydraulic fluid contained within the volume displacement chamber.

15. A device as defined in claim 13, wherein at least half of the exterior portion of the fluid pump and drive motor is contained within the volume displacement chamber.

16. A device as defined in claim 13, wherein the fluid pump and drive motor includes a proximal end in relation to the pumping chamber and a distal end, said proximal end being attached and sealed at the interconnect means, a remaining portion of the fluid pump and drive motor being housed within the volume displacement chamber.

17. A device as defined in claim 16, further comprising strain relief means positioned with respect to the distal end of the fluid pump and drive motor to prevent a wall portion which encloses the volume displacement chamber from being sucked into the fluid pump and drive motor.

18. A device as defined in claim 17, wherein the strain relief means comprises a flap attached to the distal end of the fluid pump and drive motor, said flap projecting beyond said distal end and being operable to restrain movement of the wall portion of the displacement chamber from collapsing against the distal end during systole.

19. A device as defined in claim 13, wherein the interconnect means comprises a tubular interconnect which is flexible and has sufficient length to permit placement of the ventricle in proximity to a patient's cardiac cavity and the volume displacement chamber in the area of a patient's thorax or abdomen.

20. A device as defined in claim 19, wherein the fluid pump and drive motor are positioned within a casing which has an outer diameter slightly smaller than an inner diameter of the tubular interconnect, said casing being positioned and sealed at a proximal end within the tubular interconnect to provide a flow path through the tubular interconnect and fluid pump to the volume displacement chamber.

21. A device as defined in claim 13, further comprising a second ventricle and associated second interconnect means coupled to the volume displacement chamber, and further including a second fluid pump and drive motor positioned at the second interconnect means and being capable of reversible pumping action to transfer pumping fluid through the second interconnect means and between the displacement chamber and the second pumping chamber of the second ventricle, said second pump and drive motor being positioned substantially within the volume displacement chamber such that a substantial exterior portion of the second pump and drive motor is contacted by the pumping fluid contained within the volume displacement chamber.

* * * * *

UNITED STATES PATENT AND TRADEMARK OFFICE
Certificate

Patent No. 5,282,849            Patented: February 1, 1994

On petition requesting issuance of a certificate of correction of inventorship pursuant to 35 U. S. C. 256, it has been found that the above-identified patent, through error and without deceptive intent, improperly sets forth the inventorship.

Accordingly, it is hereby certified that the correct inventorship of this patent is: William Kolff, Salt Lake City, Utah; Yvo M. Smulders, Amsterdam, Netherlands; Paul D. Diegel, Sandy, Utah; James W. Long Jr., Salt Lake City, Utah; Donald B. Olsen, Salt Lake City, Utah; John W. Holfert, Bountiful, Utah; Stephen R. Topaz, Holladay, Utah; and N. Dan Bishop, Salt Lake City, Utah.

Signed and Sealed this Ninth Day of September, 1997.

JOHN G. WEISS
*Supervisory Patent Examiner*
Patent Examining Art Unit 3308

UNITED STATES PATENT AND TRADEMARK OFFICE
CERTIFICATE OF CORRECTION

PATENT NO. : 5,282,849
DATED : February 1, 1994
INVENTOR(S) : Kolff et al.

Page 1 of 1

It is certified that error appears in the above-identified patent and that said Letters Patent is hereby corrected as shown below:

<u>Column 1,</u>
Line 5, should read -- this invention was funded in part by a grant from the National Institute of Health under contract numbers: N01-HB-88106; and R01-HL-38304. --

Signed and Sealed this

Seventeenth Day of August, 2004

JON W. DUDAS
*Acting Director of the United States Patent and Trademark Office*